United States Patent
Sklar et al.

(10) Patent No.: US 6,939,316 B2
(45) Date of Patent: Sep. 6, 2005

(54) CRANIAL ORTHOSIS FOR PREVENTING POSITIONAL PLAGIOCEPHALY IN INFANTS

(75) Inventors: Frederick H. Sklar, Waxahachie, TX (US); Paul C. Hobar, Dallas, TX (US)

(73) Assignee: Infa-Safe, Inc., Dallas, TX (US)

( * ) Notice: Subject to any disclaimer, the term of this patent is extended or adjusted under 35 U.S.C. 154(b) by 0 days.

(21) Appl. No.: 10/620,070

(22) Filed: Jul. 14, 2003

(65) Prior Publication Data

US 2004/0015118 A1 Jan. 22, 2004

(51) Int. Cl.7 ................................................. A61F 5/00
(52) U.S. Cl. ........................... 602/17; 602/5; 602/74; 128/857
(58) Field of Search ................................ 602/5, 17, 18, 602/74; 128/97.1, 857; 2/410, 417–420

(56) References Cited

U.S. PATENT DOCUMENTS

| | | | |
|---|---|---|---|
| 3,171,133 A | * | 3/1965 | Steffen ............................ 2/414 |
| 4,776,324 A | | 10/1988 | Clarren |
| 4,809,690 A | * | 3/1989 | Bouyssi et al. ................ 602/74 |
| 4,982,451 A | * | 1/1991 | Graham ........................... 2/410 |
| 5,094,229 A | | 3/1992 | Pomatto et al. |
| 5,308,312 A | | 5/1994 | Pomatto et al. |
| 5,549,678 A | * | 8/1996 | Prostkoff ................... 623/17.19 |
| 5,566,407 A | | 10/1996 | Lien |
| 5,857,232 A | | 1/1999 | Mahdavi |
| 5,951,503 A | | 9/1999 | Pomatto |
| RE36,583 E | | 2/2000 | Pomatto et al. |
| 6,052,849 A | | 4/2000 | Dixon et al. |
| 6,240,570 B1 | | 6/2001 | Wu |
| 6,266,832 B1 | | 7/2001 | Ezell |
| 6,340,353 B1 | | 1/2002 | Pomatto et al. |
| 6,360,376 B1 | | 3/2002 | Carrington |
| 6,381,760 B1 | * | 5/2002 | Lampe et al. .................... 2/425 |
| 6,421,855 B2 | | 7/2002 | Mann |
| 6,423,019 B1 | | 7/2002 | Papay et al. |
| 6,428,494 B1 | | 8/2002 | Schwenn et al. |
| 6,473,923 B1 | | 11/2002 | Straub |
| 6,592,536 B1 | * | 7/2003 | Argenta ........................ 602/17 |
| 2001/0042269 A1 | | 11/2001 | Mann |
| 2002/0010408 A1 | | 1/2002 | Pomatto et al. |
| 2002/0042954 A1 | | 4/2002 | Straub |
| 2003/0145384 A1 | * | 8/2003 | Stelnicki ......................... 5/655 |
| 2004/0181854 A1 | * | 9/2004 | Primrose ......................... 2/411 |

* cited by examiner

Primary Examiner—Henry Bennett
Assistant Examiner—Amanda Wieker
(74) Attorney, Agent, or Firm—Dennis T. Griggs (57) ABSTRACT

A cranial orthosis is contoured to match the curvature of the fronto-temporal, parietal and occipital areas of an infant's cranial vault to provide protection against the acquisition of postural cranial deformities as a result of the infant's sleeping in the supine position. The orthosis is designed to be of universal fit, as determined by the infant's fronto-occipital head circumference (FOC) measurement. Moreover, the interior dimensions of the orthosis can be enlarged to accommodate growth of the infant's head without requiring replacement. The orthosis is a molded plastic appliance in the form of a shell, headband or helmet having interior surfaces that are smoothly contoured to conform in shape to the surface curvature of the occipital, temporal and parietal areas of a healthy human infant having normal cranium size, shape and symmetry. The cavity is sized to provide a close, non-interfering fit of the conformed interior surfaces in facing relation to the occipital, fronto-temporal and parietal areas of the infant's cranial vault, thereby allowing the the infant's head weight forces to spread substantially uniformly across one or more of the conformed interior surfaces while the infant is resting on a sleep surface in the supine position.

18 Claims, 5 Drawing Sheets

CRANIAL ORTHOSIS FOR PREVENTING POSITIONAL PLAGIOCEPHALY IN INFANTS

BACKGROUND OF THE INVENTION

1. Field of the Invention

This invention is related generally to medical devices for preventing and treating cranial deformities in infants. In particular, the invention is related to a protective appliance or cranial orthosis in the form of a shell, helmet or headband that fits around a baby's head, and the use of the appliance to prevent positional plagiocephaly by redirecting the compressive forces that would otherwise be imposed on soft, compliant areas of the developing cranium by the head weight of an infant lying on a sleep surface in the supine position.

2. Description of the Related Art

Cranial asymmetry (plagiocephaly) and deformations may occur from various congenital causes including premature closure of the cranial vault and/or skull base sutures (craniosynostosis), syndromal craniofacial dysostosis, intracranial volume disorders such as hydrocephalus, microcephaly or tumor, metabolic bone disorders such as rickets and birth trauma such as depressed skull fractures. Cranial deformity (cranial molding) may also be acquired in an infant as the result of compressive forces imposed by the infant's head weight on the soft, compliant occipital areas while the infant is lying on a sleep surface in the supine position. This condition typically occurs during the first twelve months of development before the cranium is fully expanded and the brain is fully developed.

Generally, plagiocephaly is characterized by unilateral occipital flattening with contralateral occipital bulging, producing a flat spot at the back of the infant's head. The flat spot and bulging make the baby's head appear to be square or box-shaped in profile. As the deformation becomes more severe there is ipsilateral forehead protrusion, contralateral forehead flattening and endocranial skull base rotation with anterior displacement of the ipsilateral ear. If not prevented or corrected during the first twelve months of development, the deformity may become permanent.

The number of infants diagnosed with plagiocephaly increased substantially shortly after the onset of the "Back-to-Sleep" campaign by the American Academy of Pediatrics (AAP) in 1992. In that campaign, the AAP recommended that infants be placed in the supine (lying on the back, face up) sleeping position in an effort to decrease the incidence of sudden infant death syndrome (SIDS), a leading cause of early infantile deaths in the United States at that time. That campaign resulted in a substantial decrease in the incidence of SIDS. However, the incidence of plagiocephaly was observed to increase significantly over the same period. This correlation suggests that positional treatment for SIDS was the probable cause of the increased incidence of infant plagiocephaly. The consensus of craniofacial practitioners is that plagiocephaly may be acquired as a result of cranial postural molding that occurs during SIDS positional treatment. That condition is now referred to as positional plagiocephaly or acquired plagiocephaly, to distinguish it from congenital plagiocephaly.

Postural molding of the newborn's skull is common, and this presents clinically as occipital flattening, referred to as acquired plagiocephaly (or brachycephaly). Although some mild asymmetrical molding of the infant's cranial vault is likely common as a result of back sleeping, some babies develop severe cranial deformities that should be corrected. These deformities are typically characterized by flattening of only one occiput. The ipsilateral ear is displaced forward. There is compensatory bulging of the contralateral occipital area, the ipsilateral high parietal vertex, the ipsilateral temporal area, and occasionally the ipsilateral forehead. Bioccipital flattening is less commonly seen. These are acquired cranial deformities, and should be distinguished from congenital cranial deformities that result from the premature closure of a cranial surture (i.e., craniosynostosis). The latter condition frequently requires craniofacial surgery in order to correct the cranial deformity.

Positional plagiocephaly (postural molding of the cranium) may be prevented by periodically repositioning (turning over) the infant's head during sleeping. The "turn-over" repositioning treatment is not difficult to accomplish. However, to be effective this technique requires careful monitoring of the baby, diligence and the close attention of parents during sleeping hours. Although this seems simple in theory, in practice it is most difficult to accomplish consistently over the treatment term, which may extend up to 12 months, because of obligations parents may have to care for other children and attend to other matters, while at the same time trying to obtain the sleep and rest needed to carry on with work and other activities.

Infants more than three months of age and those who have not responded to repositioning may be treated with a custom-made cranial torque helmet. The torque helmet, which is precisely manufactured from an exact mold of the infant's head, continuously applies pressure or torque to the cranium to correct asymmetric deformities. The corrective forces have proven effective in some cases to restore cranial symmetry by helping the growing brain to reshape the cranium while it is still soft and compliant. The torque helmet is worn continuously, day and night, and is removed only for bathing until the child is twelve months of age or older. After twelve months of age or if the deformity is severe, torque helmets are of limited value and surgical cranial re-contouring may be required.

Custom-fitted, conventional torque devices have treated these acquired cranial deformities with varying degrees of success. The success has depended in large part on the age of the patient at the time torque treatment is begun. Clinical improvement occurs most rapidly in young infants (3 to 5 months of age). Treatment with these torque devices typically requires more time in older infants. As a child's age approaches 12 months, torque treatment becomes less effective. Many craniofacial physicians feel that little is gained with a cranial orthotic device after 12 months of age. Moreover, the acquired distortion of the base of the skull, as evidenced by the forward displacement of the ear on the side of the occipital flattening, does not generally improve with torque treatment devices. The petrous pyramids of the base of the skull tend to rigidly reinforce the skull base and resist external torsion/correction of the acquired cranial deformity.

Not infrequently, infants undergoing cranial torque treatment require re-fitting and replacement of the cranial orthosis to accommodate head growth as the child develops and the cranial deformity changes (responds). Because each orthosis is custom manufactured from an exact mold of the child's head, and because each device requires follow-up and modification as the child grows and the deformity responds, these devices are expensive and beyond the reach of many families, in particular those without effective insurance coverage. Some commercial insurance companies do not reimburse for the manufacture and use of such cranial orthotic devices, because the cranial deformities are acquired and are not the result of craniosynostosis (suture fusion).

It is therefore evident that a protective appliance is very much needed for all newborns and infants, in order to prevent the development of occipital flattening as a result of postural molding. Moreover, such a protective appliance should be universally available to all infants without requiring costly procedures to custom-fit the device to the individual infant. Rather, the protective appliance should be available on an "off-the-shelf" basis, using simple measurements such as head circumference to determine appropriate sizing. Finally, the protective appliance should be safe, simple to understand and use, relatively inexpensive and easily within the means of all families, even those without insurance coverage, so that preventive care and treatment can begin immediately after birth and continue at home without professional assistance other than the usual well baby check-ups.

BRIEF SUMMARY OF THE INVENTION

The protective appliance of the present invention is a cranial orthosis that is positioned around the head of a newborn or infant under one year of age, providing a protective shell that overlaps the occiput (os occipitale), left and right temporals (os temporale) and left and right parietals (os parietale). The protective shell has a concave profile with bilateral symmetry, and its interior surface is smoothly contoured to conform to the curvature and symmetry of the underlying occiput, temporal and parietal areas of the baby's head. Positional plagiocephaly (postural molding of the cranium) is prevented by redirecting the head weight forces that would otherwise compress the soft, compliant areas of the baby's head against the sleep surface and spreading those forces substantially uniformly over the smooth, conforming interior surface of the protective shell. The compressive forces imposed by the sleep surface (e.g., a mattress) are decoupled from the soft, vulnerable areas of the baby's head and are reacted through the protective shell. This prevents the development of a deformity and allows the developing areas of the infant's head to expand freely into the smooth, contoured cavity of the protective shell and thereby obtain normal cranial symmetry during the critical first twelve months of cranial development.

The concave pocket or cavity is sized to provide a close fit, to redistribute the compressive forces of the mattress over a large surface area of the baby's cranial vault. In the preferred embodiment, the protective appliance is in the form of a concave shell made of a durable, lightweight plastic material, having a head receiving pocket bounded by a smooth interior surface that is contoured to match the complex curvature and symmetry of the occipital, parietal and temporal regions of a normal human infant of the same age and gender.

The nominal dimensions (i.e., fronto-occipital circumference) and surface curvatures that characterize the cranium of a normal human infant are well known and documented in pediatric practice. It is also well known and universally recognized that the fronto-occipital circumference measurement (forehead to occiput) in a healthy human infant varies predictably in the population according to the infant's age and gender. Thus the protective appliance of the present invention can be provided in standard, universal sizes (e.g., small, medium and large) and fitted effectively according to the age, gender and fronto-occipital circumference measurement of the infant as determined by traditional pediatric procedures.

In the preferred embodiment, the protective appliance includes a crown portion, left and right wing portions and rostral end portions. The appliance is sized to cover substantially all of the underlying occipital area. The left and right wing portions extend bilaterally from the crown portion, overlapping the left and right parietal and the left and right temporal bones. Preferably, the upper parietal and frontal regions are only partially covered by the appliance in the protective position, thus allowing good air circulation and heat transfer over most of the infant's head, while protecting the compliant occiput from focused deformation forces applied by the sleep surface.

The wing portions are terminated by rostral end portions that are spaced apart and overlap the forehead (os frontale) area. The appliance is placed on the infant's head by spreading the rostral end portions slightly and inserting the baby's head into the protective pocket, and then allowing the rostral end portions to return to their resting (un-spread) position. Because the cranium is wider across the occiput than it is across the forehead, the appliance will be retained in the protective position by the rostral end portions, which yieldably oppose separation from the relaxed, protective position. The appliance includes a stretch band of soft woven fabric material, bridging the rostral ends of the appliance across the forehead region (os frontale) in order to help stabilize the appliance in the protective position.

According to another aspect of the invention, multiple layers of soft, spongy material or fabric material cover the contoured interior surface of the protective shell. The layers can easily be peeled away and removed at intervals to allow the appliance to accommodate normal head growth.

BRIEF DESCRIPTION OF THE DRAWINGS

The accompanying drawing figures are incorporated into and form a part of the specification to illustrate the preferred embodiments of the present invention. Various advantages and features of the invention will be understood from the following detailed description taken with reference to the drawing figures in which.

DETAILED DESCRIPTION OF THE INVENTION

The specification which follows describes a cranial orthosis intended for use by newborns and infants less than one year of age that will prevent the development of postural cranial deformities as a result of the child's sleeping on his or her back. Preferred embodiments of the invention will now be described with reference to various examples of how the invention can best be made and used. Like reference numerals are used throughout the description and several views of the drawing figures to indicate like or corresponding parts.

Referring to FIG. 1, FIG. 2, FIG. 3 and FIG. 10, the cranial orthosis of the present invention is in the form of a molded plastic appliance 10, for example a shell, headband or helmet, made of a unitary plastic molding or shell for protecting the soft, compliant skull base, occiput, left and right parietal bones and left and right temporal bones from deformation as the result of compressive forces caused by head weight while the infant is sleeping in the supine (face up) position on a sleep surface, for example a mattress. The protective appliance includes a crown portion 12 covering the left and right occipital areas, left and right wing portions 14 and 16 partially overlap the parietal, temporal and frontal areas. Rostral portions 18, 20 partially overlap the infant's forehead and help hold the appliance 10 in the operative protective position.

The crown portion 12 is centrally disposed for substantially complete overlapping coverage of the left and right sides of the occipital bone. The left and right wing portions 16, 18 extend bilaterally from the crown portion and the rostral end portions 18, 20 for terminal end portions on the wings. Preferably, the wing portions 14, 16 and rostral portions 18, 20 are dimensioned to provide limited overlapping coverage, whereby the upper parietal aspects of the bones 28, temporal bones 26 and frontal area 30 are only partially overlapped by the appliance in the protective position, thus allowing good air circulation and heat transfer over most of the infant's head, while shielding the soft, compliant occiput from direct contact against the sleep surface.

Figure 5:
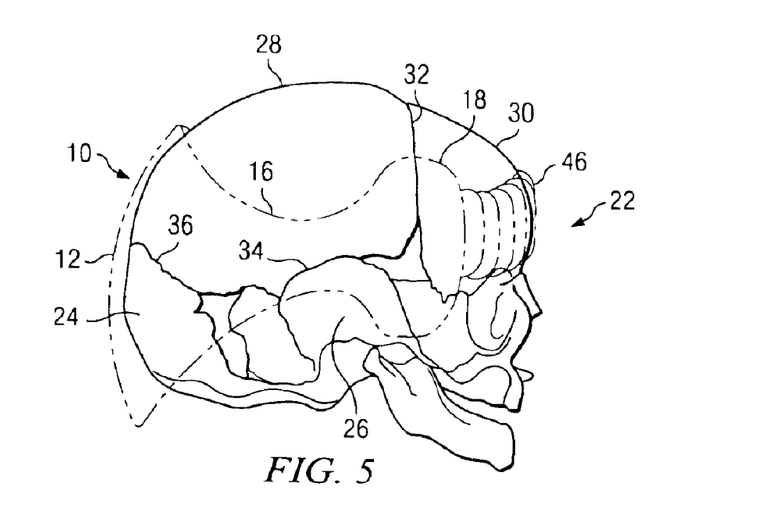
FIG. 5 is a lateral view of a human infant skull at birth showing the bones that make up the cranium and indicating in phantom the operative protective position of the cranial orthosis of the present invention.

The protective, overlapping positions of the various protective elements of the appliance 10 can best be understood with reference to FIG. 5 that shows a cranium 22 of a normal human infant. The infant cranium includes an occipital bone area 24, a temporal bone area 26, parietal bone area 28 and frontal bone area 30 that encase the brain. These bones are separated by membranous intervals 32, 34 and 36 for several months and open cranial sutures until brain growth is complete, typically until teenage years. For the first year of life, an infant's skull is soft and pliable and can be deformed or flattened by the head weight of the infant as a result of the child's sleeping on his or her back.

Figure 6:
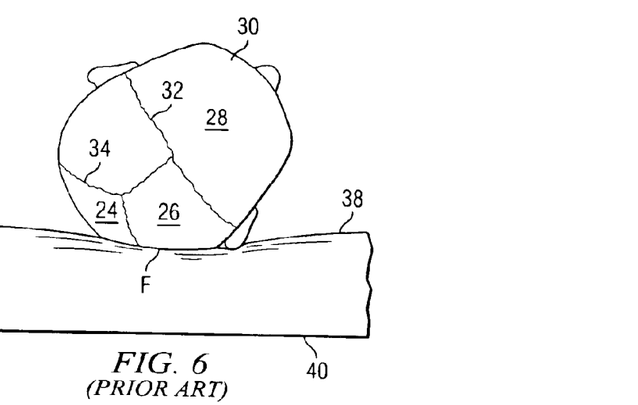
FIG. 6 is a simplified elevation view of an infant's unprotected head resting on a sleep surface in the supine position, illustrating occipital flattening that occurs as the result of forces imposed by the infant's head weight and the reaction forces imposed by the sleep surface acting to compress a relatively soft, compliant occiput.

This flattening deformity F, sometimes referred to as the "bean bag" effect, is shown in FIG. 6. Here, the soft occipital area 24 and temporal area 26 are compressed against the sleep surface 38 of a mattress 40. These soft, compliant areas deflect and are deformed inwardly along the line F, while the ipsilateral ear (and that side of the skull base) is displaced forwardly, with compensatory bulging of the contralateral occiput, the ipsilateral high parietal vertex and the ipsilateral frontal area.

Figure 7:
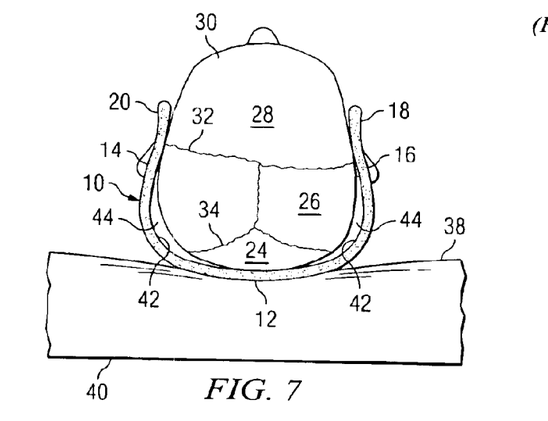
FIG. 7 is a simplified elevation view of an infant's protected head resting on a sleep surface in the supine position, illustrating the operative position of the cranial orthosis as it shields the infant's occiput.

This acquired postural deformity is prevented by the cranial orthosis 10 that includes an interior surface 42 that is conformed in shape to the surface curvature of a normal human infant cranium, thereby defining a cavity or pocket 44 for receiving the head of an infant having compliant, developing head areas to be protected. In one embodiment of the invention, the cavity 44 is sized to provide a close, non-compressive fit of the conformed interior surface 42 in facing relation to the soft developing head areas to be protected, as shown in FIG. 7 and FIG. 8.

According to another arrangement, the conformed surface 42 and protective pocket 44 are slightly oversized relative to the head of the infant, thereby providing a close but non-interfering fit of the orthosis 10 about the infant's head. In this embodiment, the contoured interior surface is positioned in facing relation to the soft developing head areas to be protected, thereby allowing the orthosis to be worn while the infant is resting on a sleep surface in a supine position substantially without focusing torque forces on one particular part of the infant's head. This arrangement allows the infant's head to turn from side-to-side without imposing binding engagement of the orthosis against the soft, developing head areas.

Figure 8:
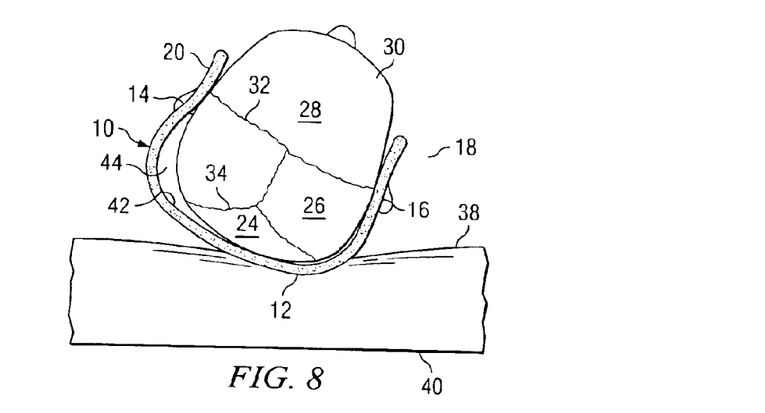
FIG. 8 is a view similar to FIG. 7 showing the infant's head in nesting engagement with cranial orthosis as it distributes the head forces uniformly over the conformed interior surface.

According to yet another arrangement, the protective pocket 44 is dimensioned to allow nesting engagement of the infant's head against the conformed interior surface 42, as shown in FIG. 8. According to this embodiment, when the infant's head is received in the protective pocket 44, the infant's head weight forces are distributed substantially uniformly across the conformed interior surface 42 that nests in engagement against one or more of the soft developing head areas while the infant is lying on a sleep surface in the supine resting position.

Figure 1:
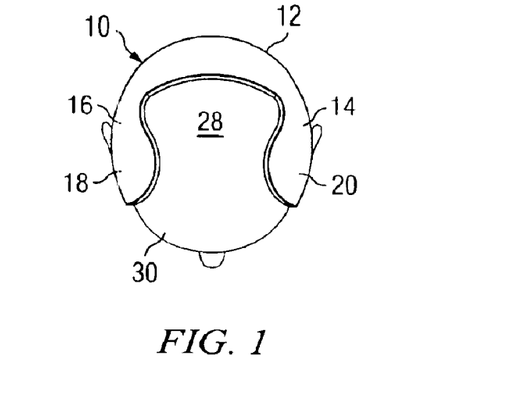
FIG. 1 is a top plan view of the cranial orthosis of the present invention fitted over the head of an infant in the protective position.
Figure 2:
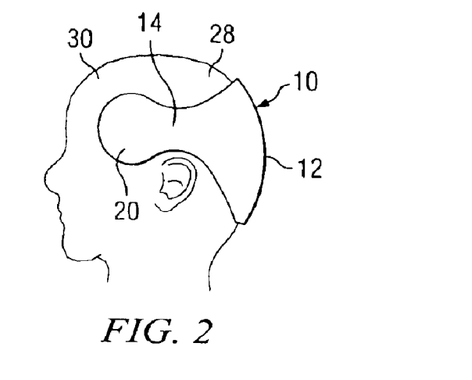
FIG. 2 is a left side elevation thereof, the right side elevation being the mirror image thereof.
Figure 3:
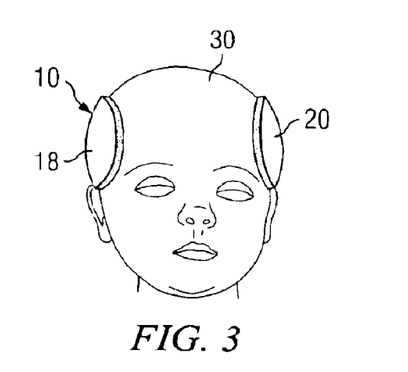
FIG. 3 is a front elevation view thereof.
Figure 4:
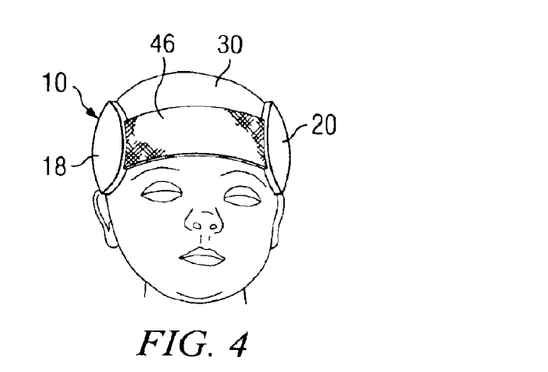
FIG. 4 is a front elevation view thereof showing a stretch headband attached to the orthosis and bridging across the forehead of the infant.

The orthosis 10 is placed on the infant's head by spreading the rostral end portions 18, 20 slightly and inserting the baby's head into the protective pocket 44, and then allowing the rostral end portions to return to their resting (un-spread) position. According to an optional embodiment as shown in FIG. 4, a stretch band 46 of soft flexible material may be connected to the rostral end portions 18, 20 and bridge across the forehead 30 of the infant when the infant's head is received in the protective pocket 44. The stretch band 46 is formed by a strip of soft, resilient material, for example woven 100% cotton fabric, broadcloth of 65% polyester and 35% cotton or open cell foam material, and is reinforced by elastic. Other materials that can be used include knitted goods, velvet-like goods, and water resistant and waterproof fabrics, such as Gore-Tex® brand fabric. The stretch band is preferred for stabilizing the slightly oversized cavity embodiment of the orthosis 10 in the protective position.

The stretch band is optional and usually is not needed because of the retaining action of the rostrals 18, 20. Because the cranium 22 is wider across the occiput than it is across the forehead, the orthosis 10 will be retained in the protective position by the rostral end portions. The rostral end portions are resilient and yieldably oppose separation, but are spreadable to allow insertion and will return automatically to the relaxed, protective position shown in FIG. 1–FIG. 3 upon release.

Figure 9:
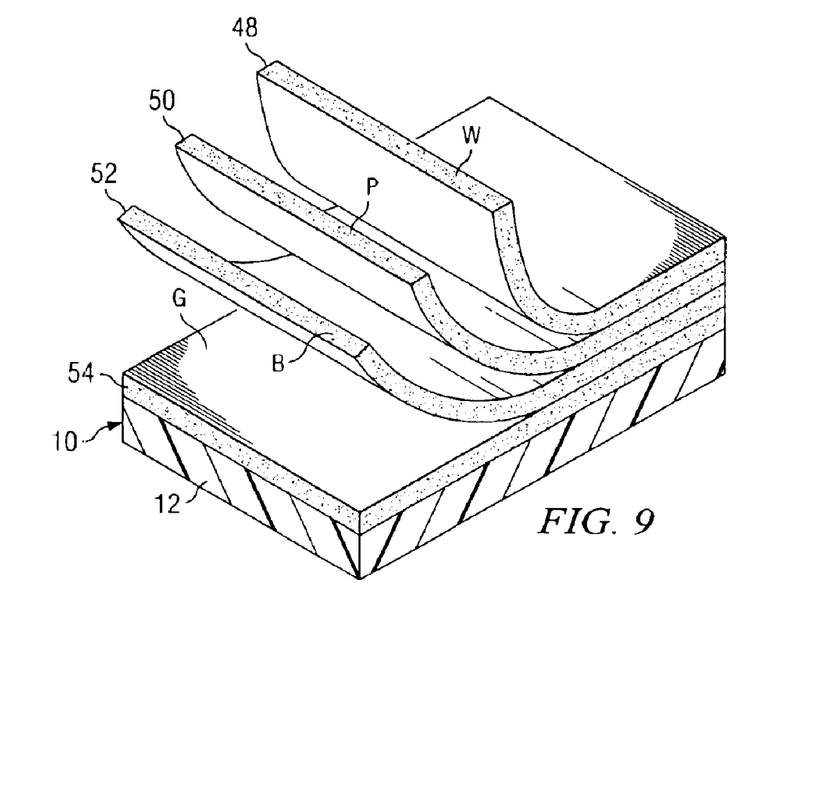
FIG. 9 is a perspective view, partially broken away, of the cranial orthosis with its conformed interior surface covered by multiple layers of soft material that can be removed independently and sequentially to accommodate head growth.
Figure 10:
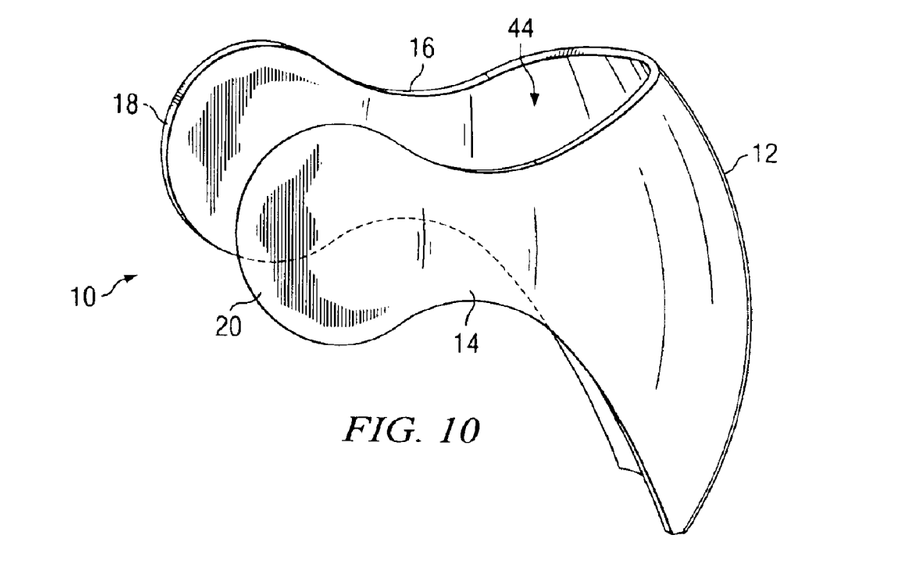
FIG. 10 is a perspective view of the cranial orthosis of the present invention.

According to another aspect of the invention, multiple layers of soft, spongy material or fabric material 48, 50, 52 and 54 cover the contoured interior surface 42 of the protective shell 12, as illustrated in FIG. 9. With the exception of the innermost base layer 54 which is permanently bonded to shell 12, the remaining layers are releasably bonded to each other by contact adhesive that permits independent release and removal of the strips one at a time. By this arrangement, the remaining layers 48, 50 and 52 can easily be peeled away and removed sequentially to accommodate normal head growth. Thus, the protective pocket 44 can be enlarged to accommodate normal growth of the infant's head, usually without requiring early replacement of the cranial orthosis 10, at least during the first three or four months.

Typically, only two orthoses may be required for most infants, to accommodate normal head growth up to 12 months of age. Premature birth infants may require three orthoses.

The protective shell 10 is molded with smooth interior surfaces that are contoured and conformed in shape to the surface curvatures of the occipital, temporal and parietal areas, respectively, of a human infant cranium having normal size, shape and symmetry of a healthy infant of a given age and gender. The nominal dimensions (i.e., fronto-occipital circumference) and surface curvatures that characterize the cranium of a normal human infant are well known and documented in pediatric practice. See, for example, the mean and standard deviation circumference values for boy infants shown in FIG. 11 and the mean and standard deviation circumference values for girl infants shown in FIG. 12, as tabulated by G. Nellhaus in Composite International and Interracial Graphs, *Pediatrics* 41: 106, 1968.

Figure 11:
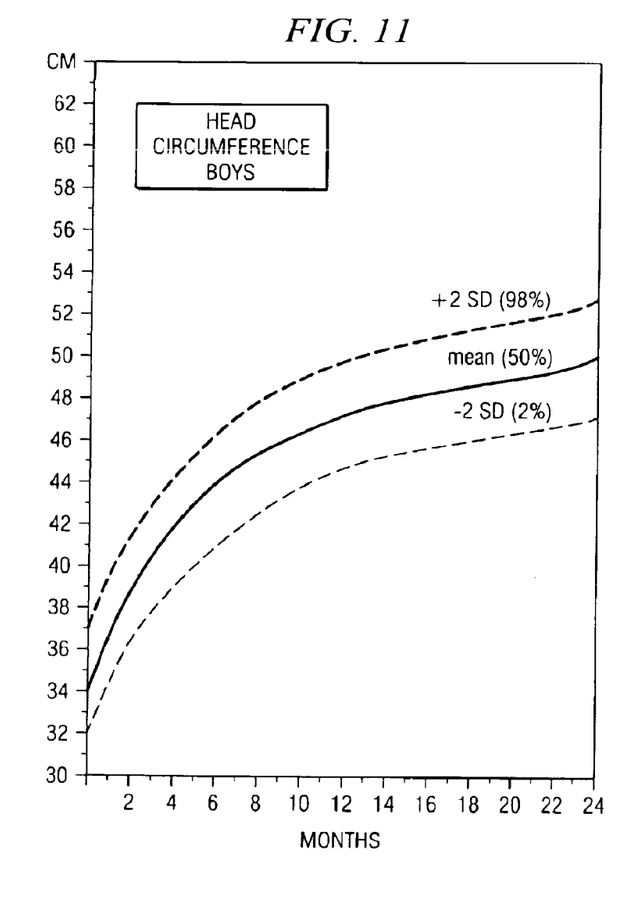
FIG. 11 is a chart that illustrates tabulated average and two standard deviation values of fronto-occipital circumference measurements for infant boys in the population age group from birth to age 24 months.
Figure 12:
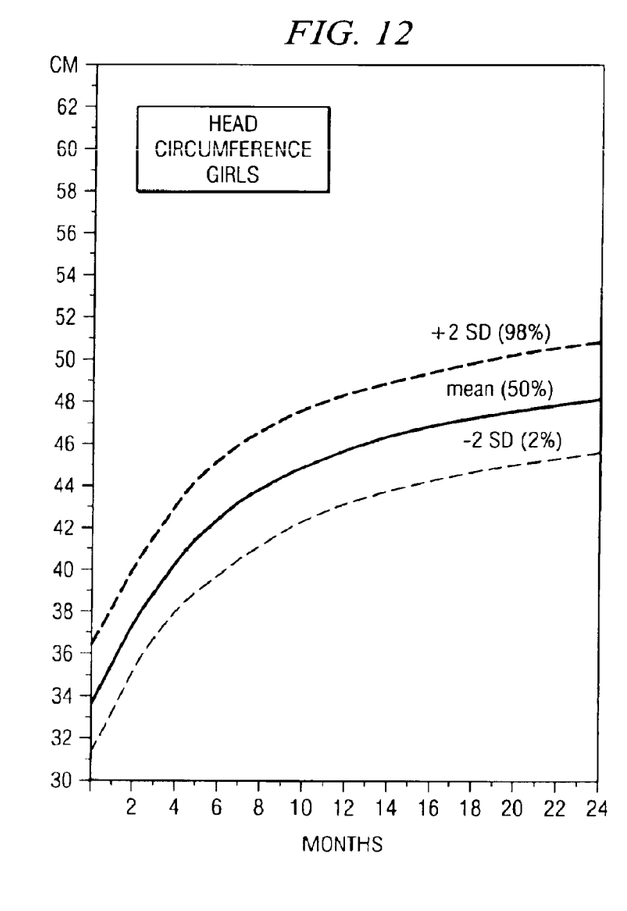
FIG. 12 is a chart that illustrates tabulated average and two standard deviation values of fronto-occipital circumference measurements for infant girls in the population age group from birth to age 24 months.
Figure 13:
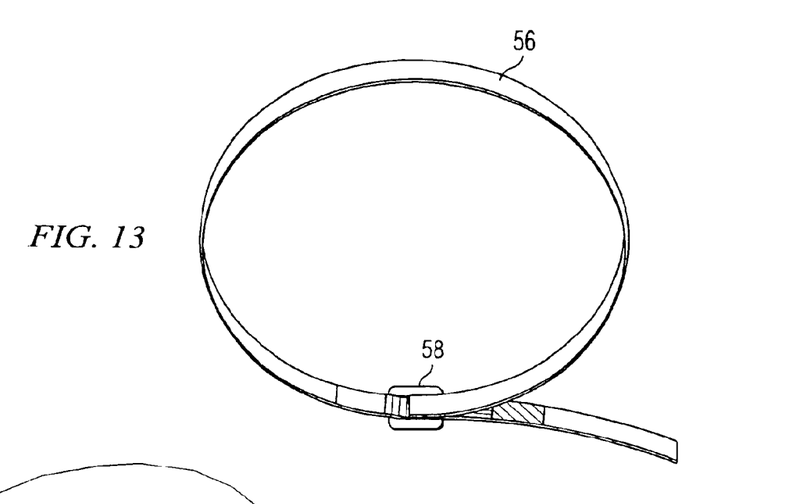
FIG. 13 is a perspective view of a flexible measuring tape used for determination of fronto-occipital circumference measurement.

It is also well known and universally recognized that the fronto-occipital circumference measurement (forehead to occiput) in a healthy human infant varies predictably in the population according to the infant's age and gender, as shown in FIG. 11 and FIG. 12. For example, during the first eighteen months of age, the mean head circumference 22 increases from about 34 to about 48 cm for boys, and from about 34 to about 47 cm for girls. Thus the protective appliance 10 can be provided in standard, universal sizes (e.g., small, medium and large) and fitted effectively according to the age, gender and fronto-occipital circumference measurement of the infant as determined by traditional pediatric procedures.

According to the method of the invention, an inventory of protective appliances 10 is established, with each appliance having a pocket conforming substantially in size and shape to the cranium of a healthy human infant of given fronto-occipital circumference (FOC) measurement. The inventory includes protective appliances of various cavity sizes that may be indexed according to age, gender and average fronto-occipital circumference values tabulated for the general infant population.

Preferably, the inventory includes multiple cranial orthosis 10 in a range of cavity sizes that may be indexed according to age, gender and average fronto-occipital circumference values corresponding to male and female mean value circumference tabulations for the general infant population. For example, the standard sizes may range in maximum circumference from about 31 centimeters (corresponding to the 2nd percentile FOC of newborn females) to about 49.5 centimeters (corresponding to 98th percentile FOC of boys at twelve months), in four or six centimeter intervals. Three or four standard or universal sizes in six or four centimeter intervals, respectively, are sufficient to span the range from birth to twelve months for a given boy or girl. A closely conforming, non-binding initial fit is easily accomplished by selecting an oversized orthotic shell 10 and lining its conformed interior surface 42 with multiple release layers 48, 50 and 52. A satisfactory fit is maintained as the infant's head grows by removing one or more of the layers from time-to-time as discussed above.

The standard size protective appliances 10 are made from control prototypes fabricated from head molds of healthy control infants having normal head size, curvature and symmetry. A control infant's head should be symmetrically shaped and free of plagiocephaly. Head growth is monitored and a set of control molds are fabricated for each control infant to provide the 2-cm FOC size increments spanning the desired range, for example from 31 centimeters to 49 centimeters for an infant boy at the 50th percentile FOC. Optionally, an overall FOC span of 18 cm can be provided by a set of two control prototypes, from which two standard over-sized protective appliances 10 are fabricated, each fitted with four or five removable layers thereby providing adjustable fit in 2-cm FOC increments over an approximate range of 9 cm each (18 cm total per set), as described below.

Plastic molds are fabricated with reference to carefully selected control infants, and from these molds control prototypes are made in two or more standard or universal sizes. The standard size protective appliances 10 are then fabricated using the control prototypes as templates and using conventional mass production manufacturing techniques, for example by pneumatic thermoforming. In the preferred embodiment of the invention, the cranial orthosis is a shell molding 10 in the form of a head band fabricated of a light weight, high impact resistant plastic such as polypropylene, high density polyethylene, acetyl or polycarbonate resin having a sidewall thickness in the range of $1/16$–$3/32$ inch.

The age and gender of the infant are known, and the fronto-occipital circumference of the infant's head is measured. With this information, a protective appliance is selected from the inventory that most closely matches the infant's head size, age and gender, which accommodates normal head growth over a specified time period. Thus a physician can prescribe a protective cranial orthosis 10 from the established inventory of standard sizes based on the simple measurement of the infant's occipital-frontal circumference (FOC) measurement.

Preferred materials for molding manufacture of the cranial orthosis 10 include engineering plastic materials such as ABS, polycarbonate, rigid polyvinyl chloride, polypropylene, acetyl, cellulose acetate butyrate, polystyrene or other high impact resistance plastic polymer resin material. For many applications more flexible plastic resins such as medium or low density polyethylene, plasticized polyvinyl chloride, polypropylene, ethylene vinyl acetate, butadiene styrene, vinyl acetate-ethylene or other suitable flexible plastic may be employed. Rigid or semi-rigid polyurethane, polyvinyl chloride, ethylene vinyl acetate, polyethylene or other suitable expandable plastic resins may also be utilized.

Figure 14:
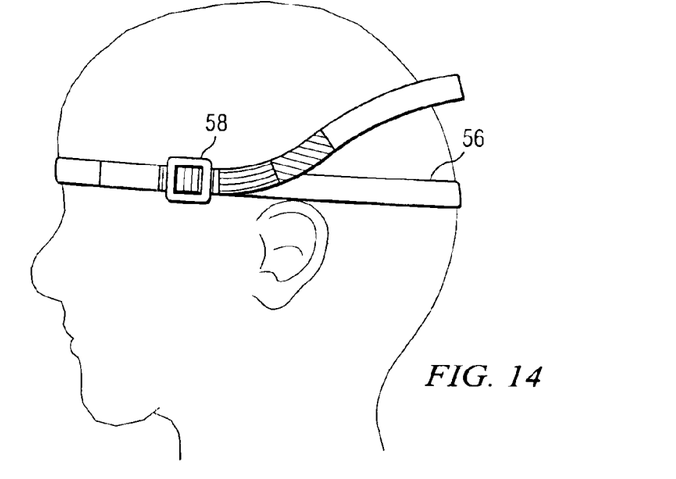
FIG. 14 is a side elevation view of the tape being applied in a fronto-occipital circumference measurement.
Figure 15:
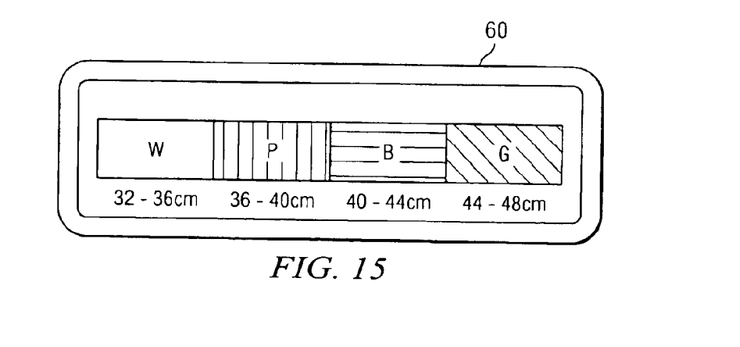
FIG. 15 is a top plan view of a color chart used as a reference for comparison with colored lining layers.

Referring now to FIG. 9, FIG. 13, FIG. 14 and FIG. 15, the removable layers 48, 50, 52 and 54 of soft fabric that cover the inner shell surface are provided in different colors, for example W (white), P(pink), B(blue) and G (green), to simplify the parents' understanding of when to remove a given layer to accommodate head growth. A flexible measuring tape 56 is fitted in a loop about the infant's head, as shown in FIG. 14 and FIG. 15, with the loop closure position of the tape buckle 58 determining the FOC. The FOC measurement is indexed with reference to colored zones on the tape, for example W (white), P (pink), B (blue) and G (green). Preferably, each colored tape segment is 2 cm in length, corresponding with the expected growth range over a predetermined interval. Alternatively, the FOC measurement is taken with reference to an external color chart 60 having color zones W, P, B and G that cross-reference the FOC increments with the colors of the various fabric lining layers. The tape measurement is taken at weekly intervals to monitor the FOC and thus determine when to remove the current lining layer. By this method the parent can easily determine the most appropriate (best fit) lining layer by matching the color indicated by the FOC tape measurement with the color of the outer-most lining layer.

It will now be appreciated that a protective cranial orthosis has been described that is capable of preventing postural plagiocephaly in infants, can be mass produced at a nominal cost per unit, and can be made universally available to all infants without requiring costly procedures to custom-fit the orthosis to the individual infant. The protective appliance 10 of the present invention can be stocked and made available on an "off-the-shelf" basis, using simple FOC head circumference measurements to select the appropriate orthosis size from an inventory of standard size appliances. Because of its simple design and construction, the protective appliance is safe, easy to understand and use, relatively inexpensive and easily within the means of all families, even those without insurance coverage, so that preventive care and treatment can begin immediately after birth and continue at home without professional assistance other than the usual well-baby check-ups. With such early treatment, disfiguring cranial deformities that are so costly to treat and sometimes impossible to correct can easily be prevented by the cranial orthosis of the present invention.

Although the invention has been described with reference to certain exemplary arrangements, it is to be understood that the forms of the invention shown and described are to be treated as preferred embodiments. Various changes, substitutions and modifications can be realized without departing from the spirit and scope of the invention as defined by the appended claims.

We claim:

1. A cranial orthosis for preventing acquired plagiocephaly in infants having a soft developing head area to be protected, comprising:

a molded appliance having an interior surface that is conformed in shape to the surface curvature of a human infant cranium and operable to accommodate infant head growth; and two or more layers of soft, flexible material releasably disposed in overlapping nested relation and lining the conformed interior surface of the appliance thereby defining a protective pocket for receiving an infant's head, the protective pocket being sized to provide a close, non-compressive fit about the developing head area to be protected such that when an infant's head is received in the protective pocket and the infant is resting on a sleep surface in a supine position, the infant's head weight forces are spread substantially uniformly across the conformed interior surface facing the developing head area, and whereby the lining layers can be removed one at a time to accommodate head growth.

2. The cranial orthosis for preventing positional plagiocephaly in infants as set forth in claim 1, wherein the contoured interior surface of the appliance is dimensioned to provide overlapping coverage over substantially all of the occipital area of the infant's head in the protective position.

3. The cranial orthosis for preventing positional plagiocephaly in infants as set forth in claim 1, the molded appliance including interior surfaces that are contoured and conformed in shape to the surface curvatures of the occipital, temporal and parietal areas, respectively, of a human infant cranium having normal size, shape and symmetry of a healthy infant of given age and gender.

4. The cranial orthosis for preventing positional plagiocephaly in infants as set forth in claim 1, characterized in that the pocket is slightly oversized relative to the head of an infant to be protected, thereby allowing the infant's head to turn from side-to-side without imposing binding engagement of the molded appliance against the developing head area.

5. The cranial orthosis for preventing positional plagiocephaly in infants as set forth in claim 1, wherein the molded appliance is loosely fitted relative to the head of an infant to be protected, whereby when an infant's head is received in the protective pocket and the infant is resting on a sleep surface in a supine position, the contoured interior surfaces provide support for the areas to be protected substantially without imposing focused torque forces on the infant's occiput.

6. The cranial orthosis for preventing positional plagiocephaly in infants as set forth in claim 1, wherein the protective pocket is sized to provide nesting engagement of the soft developing area against the layer covering the conformed interior surface, whereby when the infant's head is received in the protective pocket and the infant is resting on a steep surface in a supine position, the infant's head weight forces are distributed substantially uniformly over the covering layer that engages the soft developing area.

7. The cranial orthosis for preventing positional plagiocephaly in infants as set forth in claim 1, wherein the molded appliance is generally U-shaped in cross section and has bilateral symmetry.

8. The cranial orthosis for preventing positional plagiocephaly in infants as set forth in claim 1, wherein the molded appliance comprises a unitary molding formed of a plastic resin material.

9. The cranial orthosis for preventing positional plagiocephaly in infants as set forth in claim 1, wherein the molded appliance comprises a headband formed of a plastic resin material.

10. The cranial orthosis for preventing positional plagiocephaly in infants as set forth in claim 1, wherein the molded appliance comprises a helmet formed of a plastic resin material.

11. The cranial orthosis for preventing positional plagiocephaly in infants as set forth in claim 1, wherein the lining layers are provided in different colors that correspond with different fronto-occipital circumference increments.

12. A method for preventing postural plagiocephaly in a human infant having a cranium that is substantially normal in size and curvature for its age and gender, comprising the steps:

providing a protective appliance in the form of a shell, headband or helmet having an interior surface that is operable to accommodate infant head growth and contoured to conform to the head shape of a healthy human infant of the same age and gender, thereby defining a pocket for receiving the head of an infant having a soft developing area to be protected, wherein the pocket is sized to provide a close, non-interfering fit about the infant's head when the appliance is worn by the infant in a protective position in which the contoured interior surface is disposed in facing relation to the soft developing area to be protected;

lining the interior surface of the protective headband with one or more layers of soft, spongy material or fabric material;

supporting the infant's head within the protective appliance while the infant is resting on a sleep surface in the supine position; and removing one or more of the lining layers to accommodate growth of the infant's head.

13. The method for preventing postural plagiocephaly in infants as set forth in claim 12, including the steps:

(a) providing an inventory of the protective appliances, each of the appliances having a pocket conforming substantially in size and shape to the cranium of a healthy human infant of given age and gender, the inventory comprising a plurality of the protective appliances of various cavity sizes that are indexed according to age, gender and average fronto-occipital circumference values tabulated for the general infant population;

(b) measuring the fronto-occipital circumference of the infant's head; and (c) selecting for the infant's treatment a protective appliance from the inventory that most closely matches the infant's head size, age and gender.

14. The method for preventing postural plagiocephaly in infants as set forth in claim 12, including the step:

allowing the infant's head weight forces to spread substantially uniformly across the facing portion of the conformed interior surface lining that is engaged by the soft developing areas while the infant is in the supine position.

15. The method for preventing postural plagiocephaly in infants as set forth in claim 12, wherein the conformed interior surface lining forms the boundary of a protective pocket in which the infant's head is received, including the step of sizing the protective pocket to provide a closes, non-interfering fit of the conformed interior surface lining adjacent to the developing head area.

16. The method for preventing postural plagiocephaly in infants as set forth in claim 12, wherein the conformed interior surface lining forms the boundary of a protective pocket in which the infant's head is received, including the step of sizing the protective pocket to provide nesting engagement of the developing head area against the conformed interior surface lining.

17. The method for preventing postural plagiocephaly in infants as set forth in claim 12, wherein the conformed interior surface lining forms the boundary of protective pocket in which the infant's head is received, including the step of sizing the protective pocket to provide a close, non-compressive fit of the conformed interior surface lining about the developing head area.

18. The method for preventing postural plagiocephaly in infants as set forth in claim 12, wherein the conformed interior surface lining forms the boundary of a protective pocket in which the infant's head is received, including the step of sizing the protective pocket to provide a slightly oversized fit relative to the head of an infant to be protected whereby the orthosis can be worn without imposing binding engagement of the orthosis against the developing area of the infant's head.

\* \* \* \* \*